United States Patent [19]

Johnson

[11] 4,432,101
[45] Feb. 21, 1984

[54] CUSHIONING PATELLAR SUPPORT DEVICE

[76] Inventor: Betty J. Johnson, P.O. Box 453, La Grande, Oreg. 97850

[21] Appl. No.: 353,618

[22] Filed: Mar. 1, 1982

[51] Int. Cl.³ .............................. A61F 1/12; A61F 1/02
[52] U.S. Cl. ......................................................... 3/20
[58] Field of Search ................................. 3/20, 17–19, 3/2; 128/DIG. 20

[56] References Cited

U.S. PATENT DOCUMENTS

| | | | |
|---|---|---|---|
| 41,456 | 2/1864 | Weston | 3/20 |
| 1,057,562 | 4/1913 | La Point | 3/20 |
| 1,893,853 | 1/1933 | Tullis | 3/20 |
| 2,634,424 | 4/1953 | O'Gorman | 3/20 |
| 2,884,646 | 5/1959 | Alber | 128/DIG. 20 |
| 3,279,459 | 10/1966 | Schenker | 128/DIG. 20 |
| 3,671,980 | 6/1972 | Baird | 3/20 |
| 3,974,827 | 8/1976 | Bodeen | 120/DIG. 20 |

FOREIGN PATENT DOCUMENTS 175973 9/1953 Austria ........................................ 3/20

Primary Examiner—Ronald L. Frinks
Attorney, Agent, or Firm—Kolisch, Hartwell & Dickinson

[57] ABSTRACT

A generally butterfly-shaped inflatable/deflatable bag which is freely insertable in the upper front portion of a prosthesis designed to be worn by a below-the-knee amputee. The bag, when in place, and in use, extends around the front and lateral sides of the wearer's knee. Through a quick-disconnect hand-operable pump, which is coupled to the bag via a flexible tube, the user can adjust the degree of bag inflation to suit the particular circumstance.

2 Claims, 3 Drawing Figures

CUSHIONING PATELLAR SUPPORT DEVICE

BACKGROUND AND SUMMARY OF THE INVENTION

This invention pertains to the field of prosthetics, and more particularly, to an inflatable/deflatable, partially leg-encircling, patellar cushioning support device usable with a below-the-knee prosthesis.

For below-the-knee amputees who are fitted with a prosthesis, there are several important matters to consider regarding the manner in which the stump fits and is supported within the upper open end (cavity) of the prosthesis. One consideration, of course, is that with the prosthesis in a weight-bearing condition, adequate fore, rear and lateral support must be provided. Another is that such a prosthesis should be capable of providing this kind of support without producing undesirable and uncomfortable local bone pressure, and also without creating vascular or nerve-system constriction.

In the past, prosthetic devices have been proposed which include inflatable collars that seat within the upper end of a prosthesis of the type generally described—for the purpose of providing cushioning for a stump received in the prosthesis. However, these devices usually have not been capable of providing adequate weight-bearing support, while at the same time minimizing the problem of constricting vascular and nervous systems. One reason that prior-known inflatable supports, such as the kind just generally mentioned, have not worked satisfactorily, is that they completely encircle a stump, and when inflated sufficiently to provide adequate support, close so tightly upon the stump that they create undesired constriction.

A general object of the present invention is to provide a unique inflatable/deflatable air bag designed for free insertion and use within the upper open end of a below-the-knee prosthesis, which bag functions, with proper inflation, both to provide adequate standing cushioned support for a user, and to minimize the likelihood of constriction problems, such as those mentioned above.

According to a preferred embodiment of the invention, an inflatable/deflatable air bag, having what might be thought of as a butterfly-shaped perimetral outline, is proposed for fitment in the upper front portion of a below-the-knee prosthesis.

It is typical in such a prosthesis to have an upper rim which is non-uniform in height, and which, in particular, has a valley at the front side, and, rising therefrom, as one progresses toward the rear of the prosthesis, upwardly extending lateral support hills.

The air bag of the invention is shaped in such a manner that, when it is fitted in place, its upper margin generally follows the front and lateral rim portions of a prosthesis. The bag of the invention does not extend completely around the upper part of the prosthesis.

Extending from the bag is a flexible tube joined at its upper end, through a quick-disconnect, releasably lockable coupling, with a conventional hand pump that can be used selectively to inflate and deflate the bag the amount desired.

What might be thought of as the "wings" in the butterfly shape of the bag, have opposite extremeties each formed with an inwardly extending dip. These dips, with the bag in place, prevent the bag, when inflated, and when in use, from exerting excessive pressure in lateral knee-joint regions which are particularly sensitive to vascular and nervous constriction. Because of these dips, and because of the fact that the bag extends only partially around a stump received in a prosthesis, undesirable constriction is substantially completely eliminated.

The bag proposed by the invention is extremely simple and reliable in construction, and can be made in a variety of sizes to suit different circumstances. It is freely placeable in and removable from a prosthesis at the choice of the user.

These and other objects and advantages which are attained by the invention will become more fully apparent as the description which now follows is read in conjunction with the accompanying drawings.

DETAILED DESCRIPTION OF THE INVENTION

Figure 1:
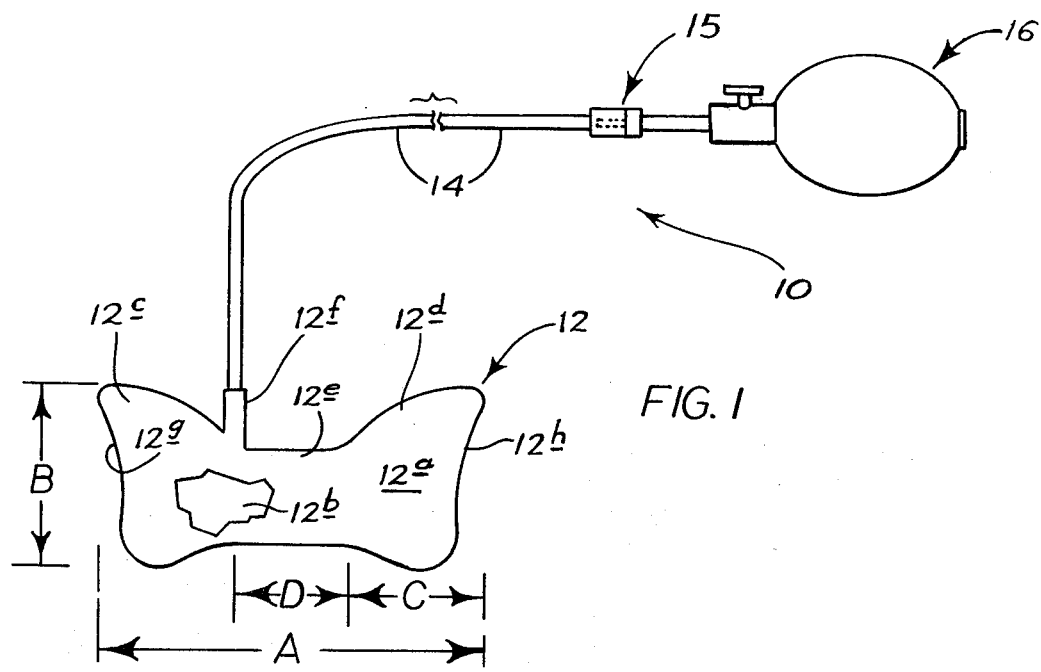
FIG. 1 is a plan view showing a cushioning patellar support device constructed in accordance with the present invention.

Turning now to the drawings, and with reference first to FIG. 1, indicated generally at 10 is a cushioning patellar support device constructed in accordance with the present invention. Device 10 includes a generally butterfly-shaped inflatable/deflatable air bag 12 having opposite sides 12a, 12b which, with the bag deflated, collapse to give the bag an extremely flat cross section. Bag 12 is made of any suitable material, such as rubber or latex, and is shaped, as shown in FIG. 1, to include a pair of wings 12c, 12d which join through a reduced-dimension neck portion 12e. While the bag of device 10 may be made in various different sizes, a typical bag sized for an adult user is illustrated here with an overall length A of about 8-inches, an overall height B of about 4-inches, with each wing having a length C of about 2¾-inches, and with neck 12e having a length D of about 2½-inches.

Extending upwardly from bag 12 in the region where wing 12c joins with neck 12e is a nipple 12f formed in the bag. Indentations, or dips, 12g, 12h define the outer margins of wings 12c, 12d, respectively.

Connecting with nipple 12f in any suitable manner, and extending upwardly therefrom, is a flexible tube, or conduit means, 14. The end of tube 14 opposite that which fits with nipple 12f is connected through a quick-disconnect, releasably lockable coupling 15 to a suitable conventional hand pump, or inflation/deflation means, 16. A coupling which has been found to perform extremely well is a so-called Luer-Lok coupling. Pump 16 may be operated in the usual manner by hand manipulation to control the amount of inflation for bag 12. As will be explained, the pump may then be disconnected in order to avoid the inconvenience of having to carry it continuously at the outer end of tube 14. Prior to such a disconnection, a suitable conventional clamp is applied to the tube, downstream from coupling 15, to prevent bag deflation.

Figure 2:
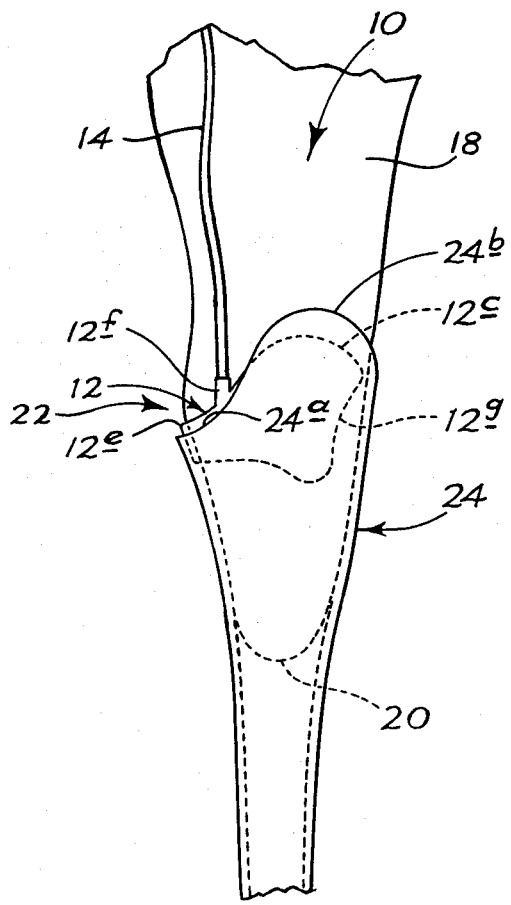
FIG. 2 is a fragmentary side view showing the device of FIG. 1 installed for use in the upper end of a below-the-knee prosthesis, with the latter receiving a stump.
Figure 3:
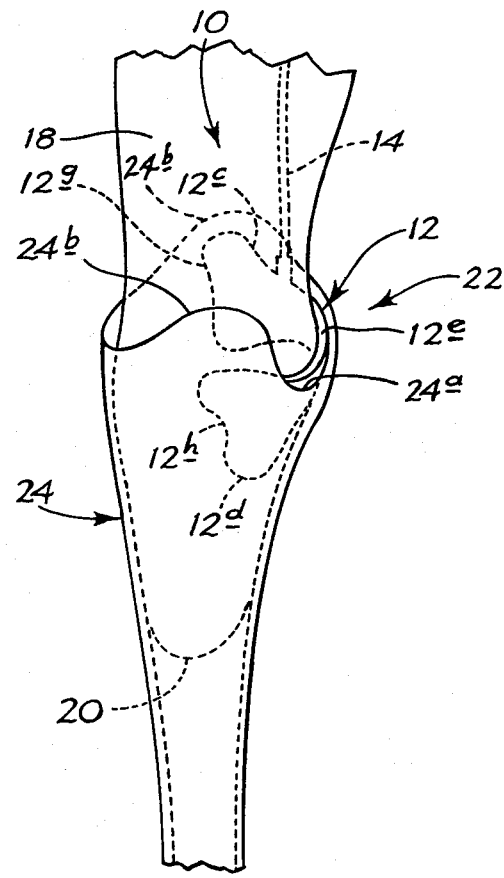
FIG. 3 is a rear top perspective view showing the same situation depicted in FIG. 2.

FIGS. 2 and 3 are each on drawn roughly the same scale as FIG. 1, and show device 10 in an operative condition. For the purpose of explanation herein, device 10 is shown in FIGS. 2 and 3 in use by a person who has had a below-the-knee amputation of his left leg. FIG. 2 is a left-side (outside) fragmentary view showing the upper leg at 18, the stump of the amputated lower leg at 20 and the knee and patellar region generally at 22. To clarify somewhat the point of view of FIG. 3, this is taken from behind the plane, and on the right side, of FIG. 2, and downwardly from a location above the knee.

In FIGS. 2 and 3, stump 20 is received within the usual upwardly facing cavity of a conventional below-the-knee prosthesis shown at 24. As can be seen, the upper rim of the prosthesis, which defines the mouth of the cavity, is formed with a front valley 24a which extends below the knee, and which joins with a pair of upwardly extending lateral hills 24b.

Bag 12 is placed freely within the prosthesis' open cavity as shown, with neck 12e extending across and generally slightly above the base of valley 24a, and with wings 12c, 12d disposed against the inside faces of hills 24b. It will be noted especially that the wings in the bag extend along the sides of the leg, but not around the back. Bag 12 is reversible, in a left-to-right direction (with respect to the way in which it is placed in the prosthesis), and in FIGS. 2 and 3 is shown with a placement whereby nipple 12f and tube 14 extend upwardly to the left outer side of the patellar region.

Explaining the use and operation of device 10, as has been suggested above, bag 10 is placed freely within the upper front part of the cavity in a prosthesis, with such tyically being done while the user is sitting down. Free rather than permanent placement of the bag allows for ready adjustment by the user to suit his or her comfort needs, and also permits free transferability of the device for use with another prosthesis if necessary. The bag is placed in the cavity in such a manner that the upper margin of neck portion 12e, with the bag inflated, provides for positive cushioned support between the rim edge in valley 24a, and the patellar region of the leg, with the user standing. This is important to prevent abrasive and direct weight-bearing contact between the prosthesis and the patellar region. In most cases, this is best accomplished by placing the bag in such a position that the upper margin of the neck portion is disposed slightly above the rim in the prosthesis' front valley. This is the condition, as mentioned above, which is illustrated in FIGS. 2 and 3.

With the user still in a sitting position, the stump is inserted in the prosthesis' cavity, and pump 16 is operated to create a slight amount of inflation for the bag. The user then stands, and further operates pump 16 to create the desired amount of bag inflation to provide for maximum support and comfort.

Since, in most instances, it would be an inconvenience to leave pump 16 connected to the upper end of tube 14, a suitable clamp is applied to the tube, downstream from coupling 15, and the coupling is disconnected to free the pump from tube 14. The pump may be carried independently, as in a hand bag or brief case, etc.

As the user walks on the prosthesis, should any change occur requiring bag inflation or deflation, it will be obvious how this readily can be accomplished.

While the situation may be different for different users, it would by typical, when a user sits and takes weight off the prosthesis, to deflate the bag somewhat so as to minimize pressure on the leg.

The wings in the bag provide for good cushioned lateral support, and the dips or indentations therein clear lateral regions in the leg which are especially prone to vascular or nervous constriction under pressure.

It will thus be apparent how the device of the invention offers all of the advantages ascribed to it earlier. It offers a user a high degree of flexibility in placement and adjustment, and is infinitely adjustable, in an inflation sense, to take care of different particular circumstances of fitment of a stump within a prosthesis.

While a preferred embodiment of the invention has been described herein, it is appreciated that variations and modifications may be made without departing from the spirit of the invention.

It is claimed and desired to secure as Letters Patent:

1. An adjustable, cushioning, non-limb-surrounding, patellar support device for use in conjunction with a prosthesis of the type designed for below-the-knee amputees, where such prosthesis includes a stump-receiving cavity defined with an upwardly facing rim having a valley portion therein at the front side of the prosthesis joined integrally with a pair of lateral-support hill portions which extend above the valley portion on opposite lateral sides of the prosthesis, said device comprising an insertable/removable, generally butterfly-shaped, flexible, inflatable/deflatable bag having enlarged, spaced wings which are joined through a central reduced-dimension neck, said bag being freely placeable within such cavity on the front side thereof, with upper marginal portions of the bag extending along a path generally following that of the above-mentioned valley and hill rim portions in the prosthesis slightly above the valley rim portion, and with opposite extremities of said wings extending to positions along the lateral sides of the prosthesis short of the back side, conduit means communicating with said bag for supplying and exhausting inflation fluid therefor, and user-manipulatable inflation/deflation means coupled for fluid communication with said conduit means, actuatable reversibly and infinitely to inflate and deflate said bag.

2. The device of claim 1, wherein each of said extremeties in said wings is formed with an inwardly extending dip.

* * * * *